United States Patent [19]
Gilchrest et al.

[11] Patent Number: 5,955,059
[45] Date of Patent: *Sep. 21, 1999

[54] USE OF LOCALLY APPLIED DNA FRAGMENTS

[75] Inventors: Barbara A. Gilchrest, Brookline; Mark Eller, Boston; Mina Yaar, Sharon, all of Mass.

[73] Assignee: Trustees of Boston University, Boston, Mass.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/467,012

[22] Filed: Jun. 6, 1995

[51] Int. Cl.$^6$ ............................. A61K 7/42; C12N 15/00; A01N 43/04
[52] U.S. Cl. ................................. 424/59; 514/44
[58] Field of Search ................ 514/44, 54, 946, 514/947; 536/23.1, 24.5; 424/450, 520, 59; 435/91.1, 6

[56] References Cited

U.S. PATENT DOCUMENTS

| | | | |
|---|---|---|---|
| 3,937,809 | 2/1976 | Jacobi | 424/60 |
| 4,419,343 | 12/1983 | Pauly | 424/59 |
| 5,470,577 | 11/1995 | Gilchrest et al. | 424/450 |

FOREIGN PATENT DOCUMENTS

| | | |
|---|---|---|
| WO93/09788 | 5/1993 | WIPO . |
| WO 93/22431 | 11/1993 | WIPO . |
| WO 95/01773 | 1/1995 | WIPO . |
| WO95/09175 | 4/1995 | WIPO . |

OTHER PUBLICATIONS

Niggli, H.J., et al., "Sunlight–Induced Pyrimidine Dimers In Human Skin Fibroblasts In Comparison With Dimerization After Artificial UV–Irradiation", Photochemistry and Photobiology, 48(3) :35–356 (1988).

Jayaraman, L. and Prives, C., "Activation of p53 Sequence–Specific DNA Binding by Short Single Strands of DNA Requires the p53 C–Terminus", Cell, 81:1021–1029 (1995).

Orkin et al. Report and recommendations of the panel to assess the NIH investment in research on gene therapy. Distributed by the National Institutes of Health, Dec. 7, 1995.

Chang, G.G. et al. Inhibition of Human Cancer Cell Growth by Periodate–oxidized 3–Aminopyridine Adenine Dinucleotide Diphosphate. Intl. J. of Bio. Chem., (1990) 22 (11) 1259–68, Jan. 31, 1990.

*Primary Examiner*—Brian R. Stanton
*Assistant Examiner*—Deborah J. R. Clark
*Attorney, Agent, or Firm*—Hamilton, Brook, Smith & Reynolds, P.C.

[57] ABSTRACT

Methods of treatment or prevention of hyperproliferative diseases or pre-cancerous conditions affecting epithelial cells, such as psoriasis, vitiligo, atopic dermatitis, or hyperproliferative or UV-induced dermatoses, and methods for reducing photoaging or for prophylaxis against or reduction in the likelihood of the development of skin cancer, are disclosed. The methods comprise administering to the cells of interest an effective amount of DNA fragments, either single- or double-stranded, or a mixture of both single- and double-stranded fragments, or deoxynucleotides, dinucleotides, or dinucleotide dimers. The DNA fragments, deoxynucleotides, dinucleotides, or dinucleotide dimers can be administered in an appropriate vehicle, such as a liposomal preparation or propylene glycol. Preparations useful in the present methods are additionally disclosed. The preparations comprise DNA fragments, either single- or double-stranded, or a mixture of both single- and double-stranded fragments, or deoxynucleotides, dinucleotides, or dinucleotide dimers, and an appropriate delivery vehicle, such as liposomes or propylene glycol.

25 Claims, 5 Drawing Sheets

USE OF LOCALLY APPLIED DNA FRAGMENTS

BACKGROUND OF THE INVENTION

Human skin consists of two layers, the dermis and the epidermis. The epidermis, which is the uppermost of the two skin layers, encompasses many different cell types, including melanocytes and keratinocytes. Melanocytes are specialized cells in the basal layer of the epidermis which synthesize melanin; the melanin is then packaged into melanosomes and then transported into keratinocytes.

Exposure of skin to the sun results in vitamin D synthesis, sunburn (erythema), and tanning, the skin's major form of endogenous protection against subsequent skin damage from ultraviolet (UV) irradiation. Various morphologic and enzymatic changes occur at the cellular level in epidermal melanocytes in response to UV irradiation. Melanin, which is increased in "tanned" skin, serves as a filter with absorbance within the UV range and provides photoprotection for the individual.

The peak action spectrum for erythema is in the UV-B range, 290–305 nm. UV-B rays are absorbed by proteins and nucleic acids of the epidermis, causing the production of thymine dimers, which are known to be formed by UV irradiation of nuclear DNA and to be excised from the DNA strand by the action of highly specific enzymes, including endonucleases. If not removed, these dimers can stall DNA replication forks generating regions of single-stranded DNA. Failure to remove thymine diners and other DNA mutations in the genome may lead to somatic mutations resulting in carcinogenesis.

In bacteria it is known that the DNA fragments released from stalled replication forks can interact with nuclear proteins which then regulate the expression of specific genes in the DNA as part of the organism's SOS response to UV damage. The tanning response of skin might reasonably be considered part of the analogous SOS response in mammalian skin. The precise stimulus for UV-induced tanning, however, remains unknown.

UV irradiation is successfully used in phototherapy and photochemotherapy for certain dermatological conditions. For example, psoriasis is a common dermatologic disease affecting 1 to 2 percent of the population. Psoriasis can be treated with UV-B irradiation, either alone or in conjunction with agents such as coal tar or anthralin, or with UV-A irradiation in combination with psoralens (PUVA therapy). Other diseases which respond to UV irradiation treatment include atopic dermatitis and vitiligo. Despite the benefits of phototherapy and photochemotherapy, these treatments carry the same risks as chronic exposure to sun, including wrinkling, "photoaging," and skin cancer.

SUMMARY OF THE INVENTION

The current invention pertains to methods of treating or preventing hyperproliferative diseases or pre-cancerous conditions affecting epithelial cells, such as psoriasis or other skin diseases, including hyperproliferative, pre-cancerous or UV-induced dermatoses. The invention further comprises methods of prophylaxis against skin cancer or reduction in the likelihood of development of skin cancer, as well as reduction of severity of photoaging resulting from sun exposure. The methods consist of applying to epithelial cells DNA fragments, either single- or double-stranded, or a mixture of both single- and double-stranded DNA fragments, or deoxynucleotides, dinucleotides, or dinucleotide dimers, such that the DNA fragments, deoxynucleotides, dinucleotides, or dinucleotide dimers are available to the cells. The fragments, deoxynucleotides or dinucleotides can be delivered topically, orally, by aerosol, or by any other appropriate means, such as by instillation. The DNA fragments, either single- or double-stranded, or the mixture of both single- and double-stranded DNA fragments, or deoxynucleotides or dinucleotides can be ultraviolet-irradiated. The method results in the stimulation of a response equivalent to that produced by sun exposure, but without the necessity of actual sun exposure, and thereby avoids subjecting the cells to the damaging and carcinogenic action of UV irradiation.

The invention also includes compositions useful in the above methods, comprising DNA fragments, deoxynucleotides, dinucleotides or dinucleotide dimers in an appropriate delivery vehicle, such as liposomes.

DETAILED DESCRIPTION OF THE INVENTION

Figure 1:
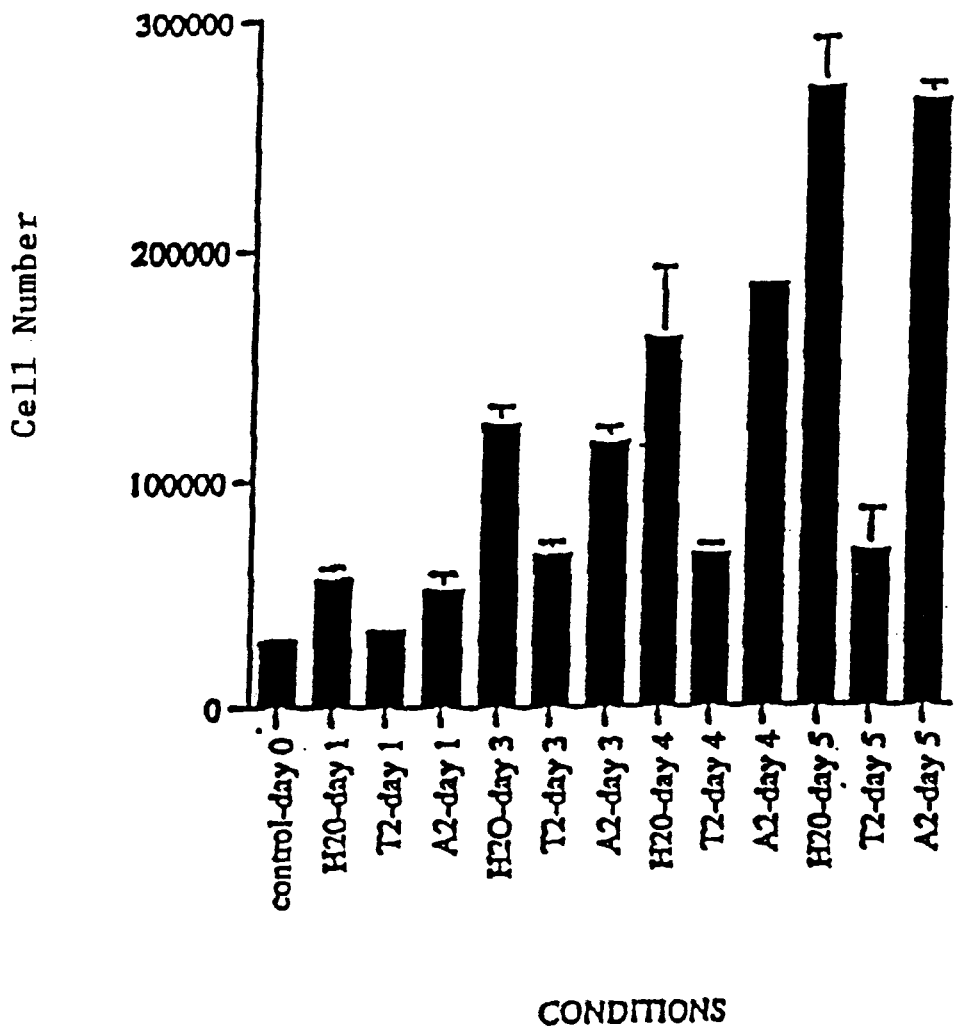
FIG. 1 is a graphic representation of the cell growth rate of human squamous carcinoma cells dosed with water (diluent), 100 $\mu$M pTpT ($T_2$) or 100 $\mu$M pdApdA ($A_2$). Day 0 is before dosage; days 1, 3, 4 and 5 are days after dosage.

The invention pertains to use of DNA fragments, deoxynucleotides, dinucleotides, or dinucleotide dimers, as defined in the following description, for the prevention or treatment of certain hyperproliferative diseases or pre-cancerous conditions affecting epithelial cells, including skin diseases such as psoriasis and hyperproliferative, pre-cancerous or UV-induced dermatoses. The invention further pertains to use of DNA fragments, deoxynucleotides, dinucleotides, or dinucleotide dimers for reduction of photoaging or prophylaxis against or reduction in the likelihood of the development of skin cancer.

The invention further provides compositions comprising said DNA fragments, deoxynucleotides, dinucleotides, or dinucleotide dimers. No exposure to sunlight is necessary for the effects resulting from the uses, methods, and compositions of the current invention.

DNA fragments of approximately 3–200 bases in length, deoxynucleotides (single bases), dinucleotides, or dinucleotide dimers, are administered in an appropriate vehicle. As used herein, "DNA fragments" refers to single-stranded DNA fragments, double-stranded DNA fragments, or a mixture of both single- and double-stranded DNA fragments. "Deoxynucleotides" refers to either a single type of deoxynucleotide or a mixture of different deoxynucleotides. "Dinucleotides" can comprise a single type of nucleotide or different types of nucleotides, and can comprise a mixture of different types of dinucleotides. In a preferred embodiment, the nucleotides of the dinucleotides are deoxynucleotides. Representative dinucleotides include $d(pT)_2$, $d(pC)_2$, $d(pA)_2$, $d(pCpT)$, $d(pTpC)$, $d(CpT)$, $d(TpC)$ and $d(TpT)$, where T is thymine, C is cytosine, d is deoxy, and p is phosphate (see Niggli, Photochem. Photobiol. 38(3):353–356 (1988)). A combination of at least two or more of DNA fragments, deoxynucleotides, dinucleotides, and/or dinucleotide dimers can also be used. The DNA fragments, deoxynucleotides, or dinucleotides can be ultraviolet-irradiated. Such ultraviolet irradiation usually results in photodimerization between two adjacent pyrimidine residues (i.e., thymine (T) and cytosine (C)) present in the DNA fragments or dinucleotides.

The DNA fragments, deoxynucleotides, dinucleotides, or dinucleotide dimers can be obtained from any appropriate source, or can be synthetic DNA fragments, deoxynucleotides, dinucleotides, or dinucleotide dimers. For example, salmon sperm DNA can be dissolved in water, and then the mixture can be autoclaved to fragment the DNA. The DNA fragments, deoxynucleotides, dinucleotides or dinucleotide dimers can be applied alone or in combination with other compounds, such as perfumes or colorants. They can be applied in a vehicle, such as water, saline, or in another appropriate delivery vehicle. The delivery vehicle can be any appropriate vehicle which promotes the delivery of the DNA fragments, deoxynucleotides, dinucleotides, or dinucleotide dimers. In one embodiment, propylene glycol is used as a delivery vehicle. In a preferred embodiment, a mixture of propylene glycol:ethanol:isopropyl myristate (1:2.7:1) containing 3% benzylsulfonic acid and 5% oleyl alcohol is used. In another embodiment, a liposome preparation is used. The liposome preparation can be comprised of any liposomes which penetrate the stratum corneum and fuse with the cell membrane, resulting in delivery of the contents of the liposome into the cell. For example, liposomes such as those described in U.S. Pat. No. 5,077,211 of Yarosh, U.S. Pat. No. 4,621,023 of Redziniak et al. or U.S. Pat. No. 4,508,703 of Redziniak et al. can be used.

The delivery vehicle can contain perfumes, colorants, stabilizers, sunscreens, or other ingredients.

The DNA fragments, deoxynucleotides, dinucleotides, or dinucleotide dimers are applied (administered) to the epithelial cells of interest in an appropriate manner. The "cells of interest", as used herein, are those cells which may become affected or are affected by the hyperproliferative disease or precancerous condition. In one embodiment, the DNA fragments, deoxynucleotides, dinucleotides, or dinucleotide dimers are applied topically to the skin surface. In other embodiments, the DNA fragments, deoxynucleotides, dinucleotides, or dinucleotide dimers are delivered orally to the oral or intestinal epithelium; by aerosol to the respiratory epithelium; by instillation to the bladder epithelium; or by other means to other cells or tissues in the body. The DNA fragments, deoxynucleotides, dinucleotides, or dinucleotide dimers are applied at an appropriate time, in an effective amount. The "appropriate time" will vary, depending on the type and molecular weight of the DNA fragments, deoxynucleotides, dinucleotides, or dinucleotide dimers employed; the condition to be treated or prevented; the results sought; and the individual patient. An "effective amount", as used herein, is a quantity or concentration sufficient to achieve the desired result. The effective amount will depend on the type and molecular weight of the DNA fragments, deoxynucleotides, dinucleotides, or dinucleotide dimers employed; the condition to be treated or prevented; the results sought; and the individual patient. For example, for the treatment or prevention of psoriasis, or for hyperproliferative, pre-cancerous, or UV-induced dermatoses, the effective amount is the amount necessary to relieve the symptoms of the disease, to reduce the area of skin affected by the disease, or to prevent the formation of affected areas. The concentration will generally be approximately 2–300 um, and will depend on the type and molecular weight of the DNA fragments, deoxynucleotides, dinucleotides, or dinucleotide dimers employed; the condition to be treated or prevented; the results sought; and the individual patient.

In a first embodiment of the current invention, DNA fragments, such as single-stranded DNA fragments, double-stranded DNA fragments, a mixture of single- and double-stranded DNA fragments, deoxynucleotides, dinucleotides, or dinucleotide dimers, are applied, either alone or in an appropriate delivery vehicle, to the epithelial cells of interest in the mammal in order to treat or prevent a hyperproliferative disease affecting epithelial cells. The DNA fragments, deoxynucleotides, dinucleotides, or dinucleotide dimers can be applied solely to affected areas, or can be applied prophylactically to regions commonly affected by the hyperproliferative disease.

In a preferred embodiment of the invention, the DNA fragments, deoxynucleotides, dinucleotides, or dinucleotide dimers are applied, either alone or in an appropriate delivery vehicle, to the epidermis for the treatment or prevention of psoriasis. The DNA fragments, deoxynucleotides, dinucleotides, or dinucleotide dimers can be applied solely to affected areas, or can be applied prophylactically to regions of epidermis commonly affected.

In another preferred embodiment of the invention, the DNA fragments, deoxynucleotides, dinucleotides, or dinucleotide dimers are applied, either alone or in an appropriate delivery vehicle, to the epidermis for the treatment or prevention of atopic dermatitis. The DNA fragments, deoxynucleotides, dinucleotides, or dinucleotide dimers can be applied solely to affected areas, or can be applied prophylactically to regions of epidermis commonly affected. In another preferred embodiment of the invention, the DNA fragments, deoxynucleotides, dinucleotides, or dinucleotide dimers are applied, either alone or in an appropriate delivery vehicle, to the epidermis for the treatment or prevention of vitiligo. The DNA fragments, deoxynucleotides, dinucleotides, or dinucleotide dimers can be applied solely to affected areas, or can be applied prophylactically to regions of epidermis commonly affected.

In another preferred embodiment, DNA fragments, deoxynucleotides, dinucleotides, or dinucleotide dimers are applied, either alone or in an appropriate delivery vehicle, to the epidermis for the treatment or prevention of other hyperproliferative, pre-cancerous or UV-induced dermatoses.

In a second embodiment, DNA fragments, deoxynucleotides, dinucleotides, or dinucleotide dimers are applied, either alone or in an appropriate delivery vehicle, to the epidermis for reduction of photoaging, or prophylaxis against or reduction in the likelihood of development of skin cancer. The DNA fragments, deoxynucleotides, dinucleotides, or dinucleotide dimers are applied at an appropriate time (i.e., sufficiently close in time to exposure of the skin to UV irradiation): the DNA fragments, deoxynucleotides, dinucleotides, or dinucleotide dimers can be applied before, during or after exposure to UV irradiation. They can be applied daily or at regular or intermittent intervals. In a preferred embodiment, the DNA fragments, deoxynucleotides, dinucleotides, or dinucleotide dimers can be applied on a daily basis to skin which may be exposed to sunlight during the course of the day.

The invention is further illustrated by the following Examples.

EXAMPLE 1

Application to Human Squamous Carcinoma Cells

Human squamous carcinoma cells line SCC12F cells were maintained in primary keratinocyte medium (300 ml DME, 100 ml F-12 nutrient supplement, 50 ml 10×Adenine, 50 ml fetal bovine serum, 5 ml penicillin/streptomycin stock, and 0.5 ml of 10 μg/ml epidermal growth factor and hydrocortisone to final concentration of 1.4 μg/ml) and dosed with either water (diluent), 100 μM pTpT ($T_2$) or 100 μM pdApdA ($A_2$). Cells were harvested before dosing (day 0), and 1, 3, 4, and 5 days after dosage, and were counted by Coulter counter. After harvesting, the cells were processed for total RNA isolation and were analyzed by Northern blot.

Addition of pTpT ($T_2$) to human squamous carcinoma cells resulted in marked decreases in cell growth rate, as shown in FIG. 1. Addition of a control deoxyadenine dinucleotide (pdApdA or $A_2$), a compound very similar to pTpT but not readily dimerized by UV irradiation and therefore not excised during the course of UV-induced DNA repair, has no effect (A).

Addition of thymidine dinucleotides ($T_2$) to human squamous carcinoma cells for 24–72 hours resulted in upregulation of at least three genes: growth arrest and DNA damage (GADD 45), senescence-derived inhibiter (Sdi I), and excision repair cross-complementing (ERCC-3) (data not shown). Compared to the diluent ($H_2O$) control, the inductions were most prominent at 72 hours, but detectable also at 24 and 48 hours. Addition of the control deoxyadenine dinucleotide ($A_2$) was less effective or ineffective in inducing these genes. Comparable data have been obtained in preliminary experiments with S91 melanoma cells. The time course of induction is similar to that observed after UV irradiation for the two genes for which this has been studied (GADD 45 and Sdi I) (Fornace, A. J. et al., Proc. Natl. Acad. Sci. USA 85:8800–8804 (1988); Hollander, M. C. et al., J. Biol. Chem. 268:24385–24393 (1993); Zhan, Q. et al., Mol. Cell Biol. 14:2361–2371 (1994); El-Deiry, W. S. et al., Cancer Res. 54:1169–1174 (1994); and El-Deiry, W. S. et al., Cell 75:817–825 (1993)) and also similar to the time course of induction of the tyrosinase gene by $T_2$ in melanocytes and melanoma cells (Maltzman, W. and L. Czyzyk, Mol. Cell Biol. 4:1689–1694 (1984); and Lu, X. and D. P. Lan, Cell 75:765–778 (1993)). Sdi I is known to be involved in cell cycle regulation and specifically in blocking cell division. GADD 45 and ERCC-3, a human DNA repair enzyme, are known to be involved in repair of UV-induced DNA damage.

The response to pTpT is identical to that observed after UV irradiation of these cell lines, and is also similar to the response to various antimetabolites, such as methotrexate, that are clinically effective in the treatment of hyperproliferative skin disorders.

EXAMPLE 2

Application to Human Cervical Carcinoma Cells

Human cervical carcinoma cells (HeLa cells) were maintained in DMA+10% calf serum and dosed with either water (diluent) or 100 μM pTpT (T2). Cells were collected 1, 4 and 6 days after dosage and counted by Coulter counter.

Figure 2:
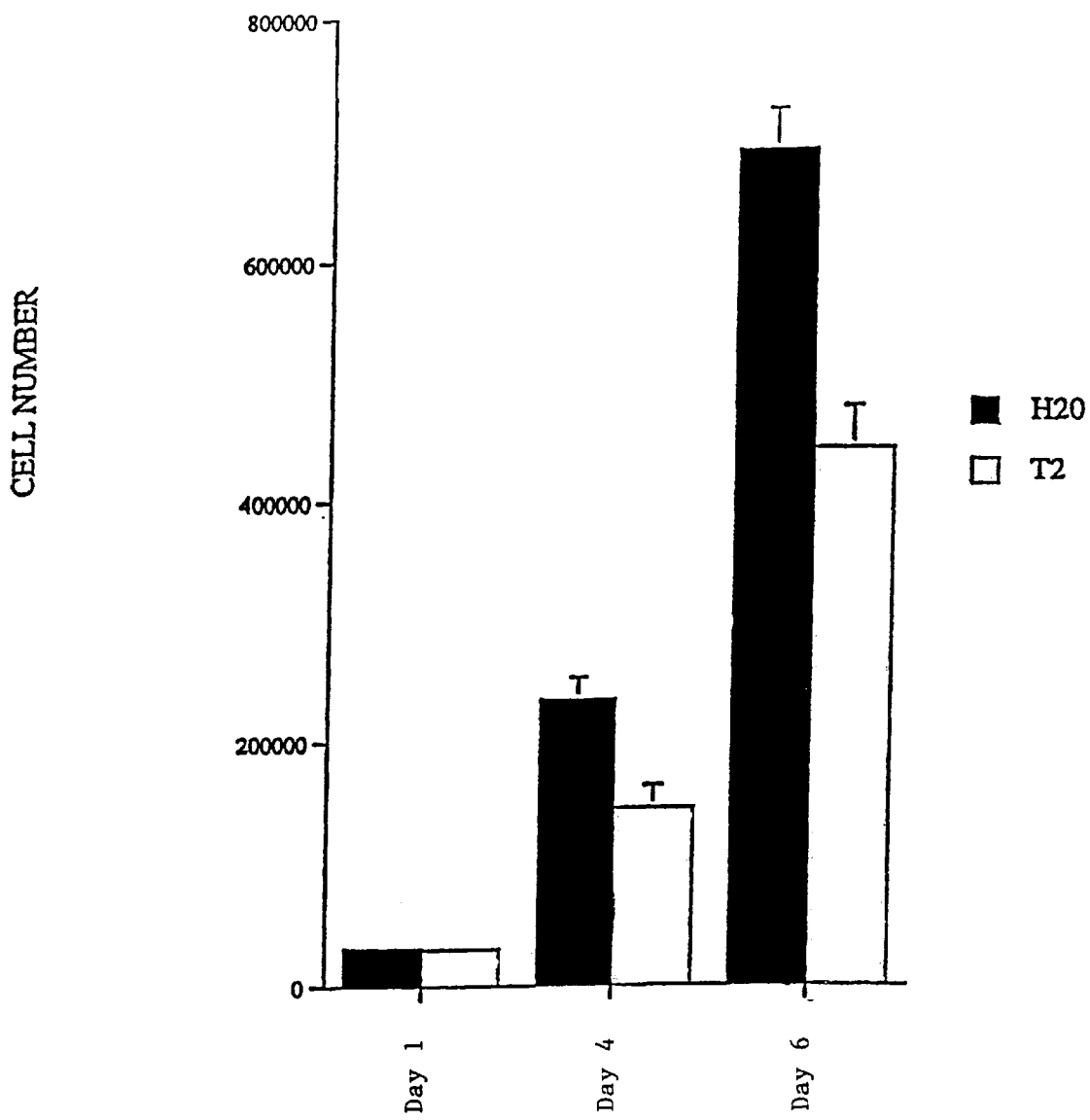
FIG. 2 is a graphic representation of the cell growth rate of human cervical carcinoma cells dosed with either water (diluent) or 100 $\mu$M pTpT ($T_2$). Day 0 is before dosage; days 1, 4 and 6 are days after dosage.

Addition of pTpT ($T_2$) to the human cervical carcinoma cells resulted in marked decreases in cell growth rate, as shown in FIG. 2.

EXAMPLE 3

Application to Human Melanoma Cells

Human melanoma cell lines CRL 1424, Malma, Sk Mel 2, and Sk Mel 28 were obtained from the American Type Culture Collection (ATCC). The cell lines were maintained in DME+2% calf serum, and dosed with either water (diluent) with DME, or 100 μM pTpT (T2) in DME. One week after dosage, cells were collected and counted by Coulter counter.

Figure 3:
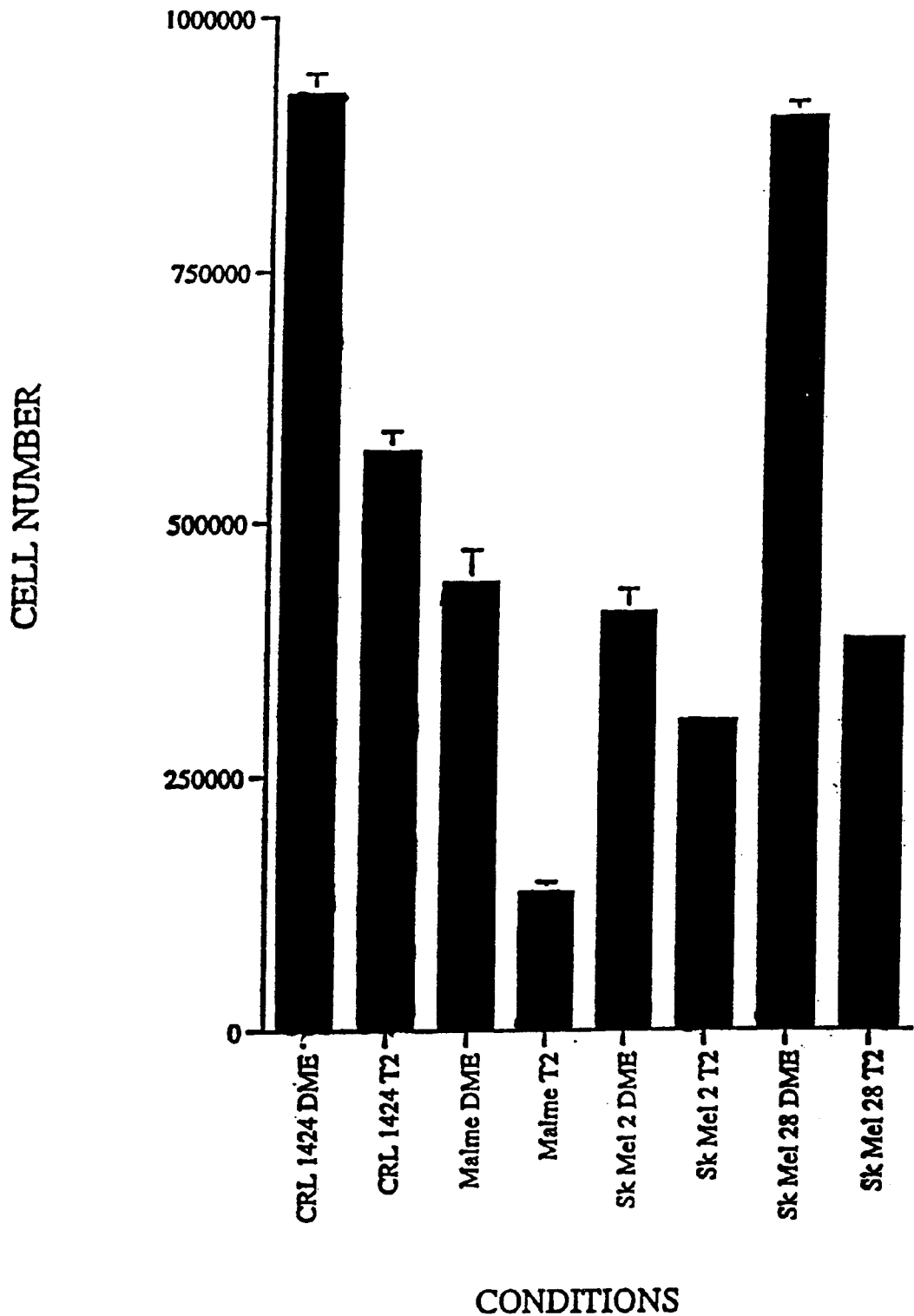
FIG. 3 is a graphic representation of the cell yield of human melanoma cell lines dosed with either diluent or 100 $\mu$M pTpT ($T_2$).

Addition of pTpT ($T_2$) to any of the four different human melanoma cell lines results in marked decreases in cell yields, as shown in FIG. 3.

EXAMPLE 4

Application to Human Keratinocytes

Figure 4:
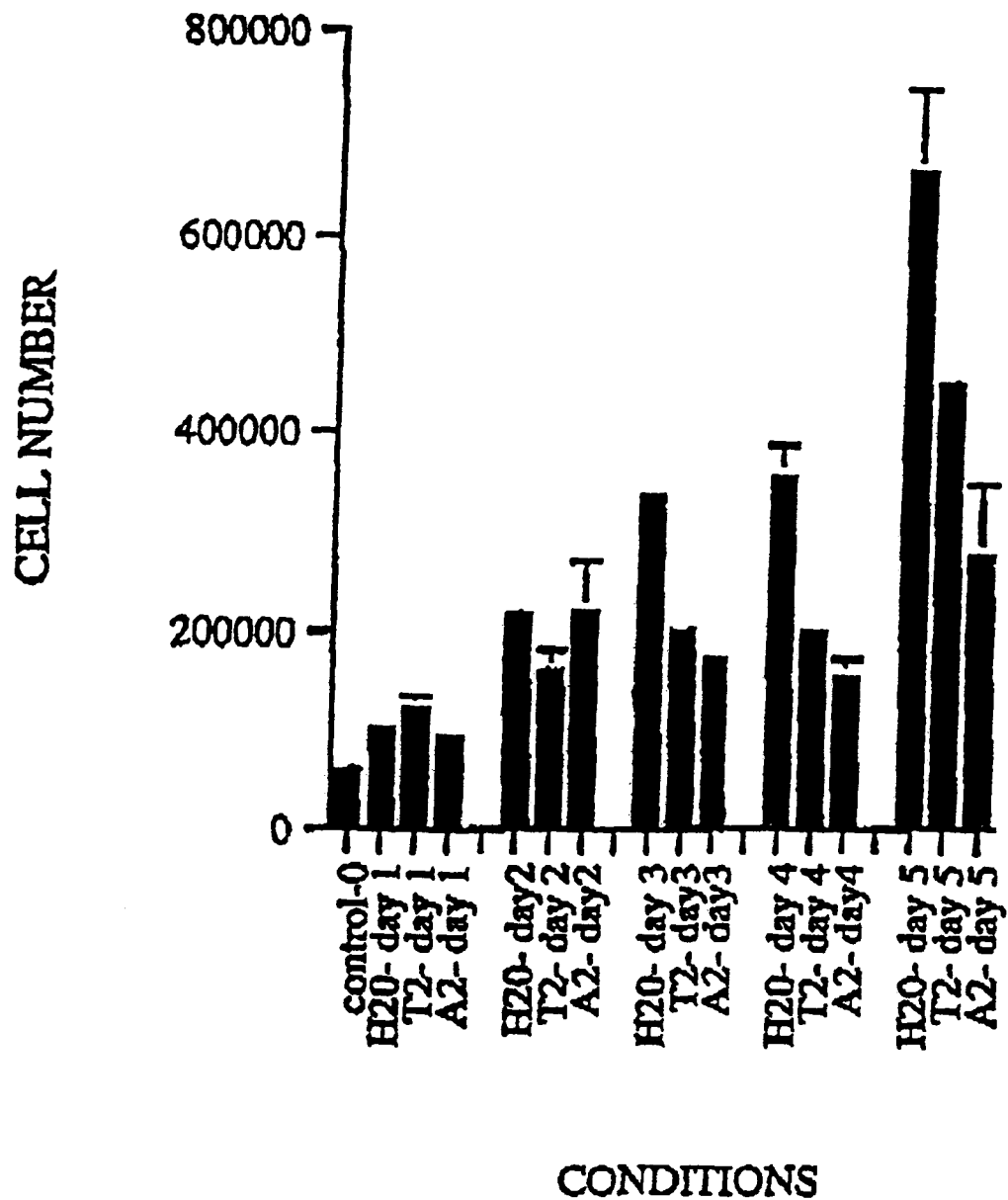
FIG. 4 is a graphic representation of the average cell number of human neonatal fibroblasts dosed with either water, $T_2$ or $A_2$.
Figure 5:
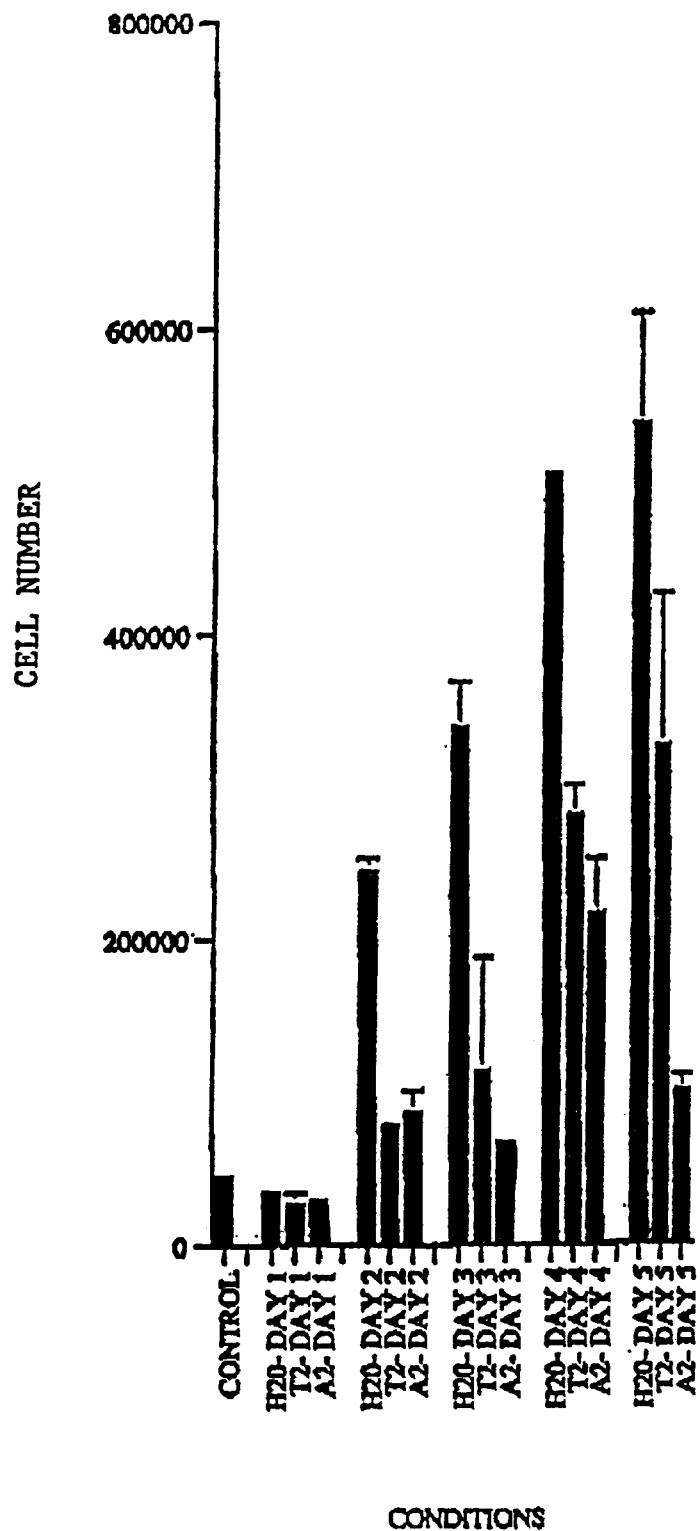
FIG. 5 is a graphic representation of the average cell number of human neonatal fibroblasts dosed with either water, $T_2$ or $A_2$.

Northern blot analysis of normal human keratinocytes treated with pTpT for 24–72 hours that shows induction of the tumor necrosis factor (TNF) alpha gene (data not shown). This immunomodulatory cytokine, known to be induced by UV irradiation, may thus be induced by pTpT. Use of locally applied DNA fragments, deoxynucleotides, dinucleotides, or dinucleotide dimers may therefore be useful in immunomodulation of cutaneous reactions and in treatment or prevention of diseases or conditions involving immunomodulation. FIGS. 4 and 5. The results indicate that application of the DNA fragments inhibits cell multiplication.

EXAMPLE 6

Effect of pTpT Applications on Epidermal Labeling Index

Guinea pigs received one or two daily topical applications of 100 μM pTpT, or vehicle alone as control, for three days. On the fourth day, punch biopsies were obtained and maintained for 7 or 8 hours in primary keratinocyte medium supplemented with 10 uCi/ml $^3$H-thymidine (specific activity 9.0 Ci/m mole, NEN). Tissues were then rinsed with cold medium and fixed in 10% phosphate buffered formalin. After a series of dehydration steps, tissues were embedded in paraffin. 6 um sections were cut and mounted onto glass slides, dipped in NTB-2 Nuclear Track emulsion and kept in the dark at 4° C. for 7 days. Sections were developed in Kodak D-19 developer and stained with hematoxylin and eosin. Labeling index was measured by calculating the percentage of labeled nuclei among 100 basal keratinocytes.
Results

| | Labeling Index | |
|---|---|---|
| Vehicle control | pTpT | |
| | 2 daily applications | |
| 4 ± 1.4 | 1.5 ± 0.7 | |
| | 1 daily application | |
| 4.5 ± 2.1 | 2 ± 0 | |

Results±SD are shown

Labeling index (a measure of epidermal turnover rate) is less in pTpT-treated skin than in vehicle-treated skin, (>0.03 paired T test) in both experiments. These results demonstrate that the DNA fragments reduce epidermal turnover rate.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

What is claimed is:

1. A method of treating psoriasis in a mammal, comprising administering topically to the epidermis of the mammal an effective amount of DNA fragments such that administration results in an inhibition of proliferation of the cells of interest or a decrease in epidermal thickness; and wherein said DNA fragments are approximately 2–200 bases in length, the DNA fragments being selected from the group consisting of: single-stranded DNA fragments, double-stranded DNA fragments, and a mixture of single- and double-stranded DNA fragments.

2. The method of claim 1, wherein the topical administration is by aerosol.

3. The method of claim 1, wherein the DNA fragments are dinucleotides selected from the group consisting of: $d(pT)_2$, $d(pC)_2$, $d(pA)_2$, $d(pCpT)$, $d(pTpC)$, $d(CpT)$, $d(TpC)$ and $d(TpT)$.

4. The method of claim 1, wherein said deoxynucleotides or dinucleotides are ultraviolet-irradiated.

5. The method of claim 1, wherein the DNA fragments are dinucleotide dimers selected from the group consisting of: $d(pT)_2$, $d(pC)_2$, $d(pA)_2$, $d(pCpT)$, $d(pTpC)$, $d(CpT)$, $d(TpC)$ and $d(TpT)$.

6. A method of treating vitiligo in a mammal, comprising administering topically to the epidermis of the mammal an effective amount of DNA fragments; and wherein said DNA fragments are approximately 2–200 bases in length, the DNA fragments being selected from the group consisting of: single-stranded DNA fragments, double-stranded DNA fragments, and a mixture of single- and double-stranded DNA fragments.

7. The method of claim 6, wherein the topical administration is by aerosol.

8. The method of claim 6, wherein the DNA fragments are dinucleotides selected from the group consisting of: $d(pT)_2$, $d(pC)_2$, $d(pA)_2$, $d(pCpT)$, $d(pTpC)$, $d(CpT)$, $d(TpC)$ and $d(TpT)$.

9. The method of claim 6, wherein said deoxynucleotides or dinucleotides are ultraviolet-irradiated.

10. The method of claim 6, wherein the DNA fragments are dinucleotide dimers selected from the group consisting of: $d(pT)_2$, $d(pC)_2$, $d(pA)_2$, $d(pCpT)$, $d(pTpC)$, $d(CpT)$, $d(TpC)$ and $d(TpT)$.

11. A method of reducing photoaging in a mammal, comprising administering topically to the epidermis of the mammal an effective amount of DNA fragments that are approximately 2–200 bases in length, the DNA fragments being selected from the group consisting of: single-stranded DNA fragments, double-stranded DNA fragments, and a mixture of single- and double-stranded DNA fragments.

12. The method of claim 11, wherein the DNA fragments are dinucleotides selected from the group consisting of: $d(pT)_2$, $d(pC)_2$, $d(pA)_2$, $d(pCpT)$, $d(pTpC)$, $d(CpT)$, $d(TpC)$ and $d(TpT)$.

13. The method of claim 11, wherein said deoxynucleotides or dinucleotides are ultraviolet-irradiated.

14. The method of claim 11, wherein the DNA fragments are dinucleotide dimers selected from the group consisting of: $d(pT)_2$, $d(pC)_2$, $d(pA)_2$, $d(pCpT)$, $d(pTpC)$, $d(CpT)$, $d(TpC)$ and $d(TpT)$.

15. A method of reducing the susceptibility to UV-induced hyperproliferative disease in a mammal, comprising administering topically to the epidermis of the mammal an effective amount of DNA fragments that are approximately 2–200 bases in length, the DNA fragments being selected from the group consisting of: single-stranded DNA fragments, double-stranded DNA fragments, and a mixture of single- and double-stranded DNA fragments.

16. The method of claim 15, wherein the topical administration is by aerosol.

17. The method of claim 15, wherein the DNA fragments are dinucleotides selected from the group consisting of: $d(pT)_2$, $d(pC)_2$, $d(pA)_2$, $d(pCpT)$, $d(pTpC)$, $d(CpT)$, $d(TpC)$ and $d(TpT)$.

18. The method of claim 15, wherein said deoxynucleotides or dinucleotides are ultraviolet-irradiated.

19. The method of claim 15, wherein the DNA fragments are dinucleotide dimers selected from the group consisting of: $d(pT)_2$, $d(pC)_2$, $d(pA)_2$, $d(pCpT)$, $d(pTpC)$, $d(CpT)$, $d(TpC)$ and $d(TpT)$.

20. A method of inhibiting UV-induced dermatoses in a mammal, comprising topically administering, to the epidermal epithelial cells of interest in the mammal an effective amount of DNA fragments that are approximately 2–200 bases in length, the DNA fragments being selected from the group consisting of: single-stranded DNA fragments, double-stranded DNA fragments, and a mixture of single- and double-stranded DNA fragments.

21. The method of claim 20, wherein the DNA fragments are dinucleotides selected from the group consisting of: $d(pT)_2$, $d(pC)_2$, $d(pA)_2$, $d(pCpT)$, $d(pTpC)$, $d(CpT)$, $d(TpC)$ and $d(TpT)$.

22. The method of claim 20, wherein said deoxynucleotides or dinucleotides are ultraviolet-irradiated.

23. The method of claim 20, wherein DNA fragments are dinucleotide dimers selected from the group consisting of: $d(pT)_2$, $d(pC)_2$, $d(pA)_2$, $d(pCpT)$, $d(pTpC)$, $d(CpT)$, $d(TpC)$ and $d(TpT)$.

24. The method of claim 20, wherein the topical administration is by aerosol.

25. A method of reducing the susceptibility to skin cancer in a mammal, comprising administering topically to the epidermis of the mammal an effective amount of DNA fragments that are approximately 2–200 bases in length, the DNA fragments being selected from the group consisting of: single-stranded DNA fragments, double-stranded DNA fragments, and a mixture of single- and double-stranded DNA fragments.

* * * * *